United States Patent [19]

Rost

[11] Patent Number: 4,680,967

[45] Date of Patent: Jul. 21, 1987

[54] ULTRASONIC ANGLE TEST PROBE HAVING AT LEAST TWO TRANSDUCERS

[75] Inventor: Manfred Rost, Wesseling, Fed. Rep. of Germany

[73] Assignee: Krautkramer-Branson, Incorporated, Lewistown, Pa.

[21] Appl. No.: 862,140

[22] Filed: May 12, 1986

[30] Foreign Application Priority Data

Sep. 24, 1985 [DE] Fed. Rep. of Germany ....... 3534002

[51] Int. Cl.$^4$ ............................................. G01N 29/04
[52] U.S. Cl. ...................................... 73/628; 73/644; 310/336
[58] Field of Search ................ 73/628, 632, 6411, 644; 310/336

[56] References Cited

U.S. PATENT DOCUMENTS 3,100,987 8/1963 Bincer .................................. 73/644
4,435,984 3/1984 Gruber ................................. 73/628

Primary Examiner—Stewart J. Levy
Assistant Examiner—John E. Chapman, Jr.
Attorney, Agent, or Firm—Philip J. Feig

[57] ABSTRACT

This invention relates to an ultrasonic angle test probe comprising at least two ultrasonic transducers for respectively generating and receiving ultrasonic waves propagating in different directions. According to the invention, in order to obtain relatively small wedge shaped coupling members and small coupling surfaces on the side of the probe contacting the workpiece, a plurality of transducers are disposed above one another instead of side by side. In a typical embodiment, a first transducer is disposed on a first wedge-shaped coupling member and second transducer is disposed on a second wedge-shaped coupling member superposed upon said first coupling member for providing different angles of propagation of sound waves responsive to energizing one or the other transducer.

2 Claims, 2 Drawing Figures

ULTRASONIC ANGLE TEST PROBE HAVING AT LEAST TWO TRANSDUCERS

BRIEF SUMMARY OF THE INVENTION

This invention relates to an ultrasonic angle test probe comprising at least two ultrasonic transducers for respectively generating and receiving ultrasonic signals propagating in different directions, the first ultrasonic transducer being disposed on a first wedge-shaped coupling element.

Test probes of this type are known; see for instance DE-OS No. 30 35 463. The individual ultrasonic transducers are disposed at different angles on the same coupling element of the test probe. Very large coupling elements are needed, particularly when using relatively large area transducers, as is required for large near-field lengths. Frequently the individual transducers are associated with different sound exit surfaces on the side of the test probe facing the workpiece, so that the coupling conditions may vary as a function of the transducer used.

It is also known as disclosed in DE-OS No. 22 27 198 to use only a single rotatably mounted transducer instead of securing a number of transducers to a coupling element at different angles. These arrangements require a relatively expensive rotatable frame. Finally, U.S. Pat. No. 4,458,534 dated July 10, 1984, issued to J. Kising, discloses an angle test probe where a lens bearing an array transducer is disposed in the coupling element. The direction of propagation of the sound waves varies depending on which of the elements in the array are actuated. This test probe arrangement is relatively expensive and not suited for many applications.

An object of this invention, therefore, is the provision of an angle test probe having a plurality of transducers for providing ultrasonic waves at different angles and including means for keeping the coupling elements and coupling surfaces small even when large area transducers are used.

The basic principle of the invention is solved by disposing a number of transducers on top of one another instead of side by side, using wedge-shaped coupling members, and taking advantage of the differences in the propagation angles of the corresponding ultrasonic waves.

Other details and advantages of the invention will be described in greater detail with reference to embodiments shown in the drawings.

DETAILED DESCRIPTION OF THE INVENTION

Figure 1:
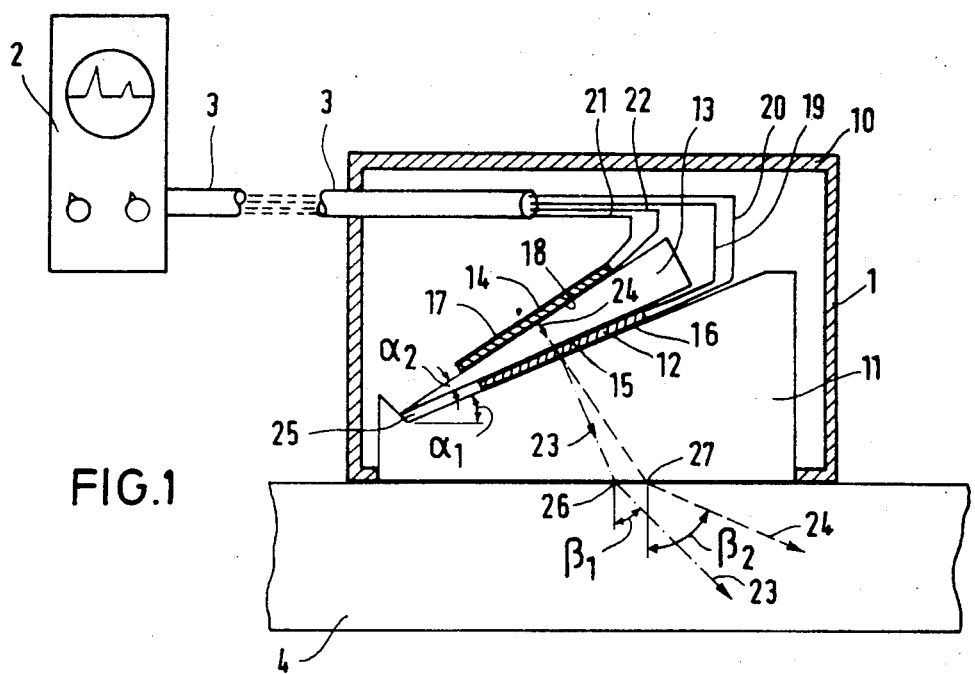
FIG. 1 is an elevational view, partly in section, of the angle probe according to the invention.

With reference to FIG. 1, an ultrasonic angle probe 1 is electrically connected via a cable 3 to an ultrasonic test instrument 2 and is acoustically coupled to a workpiece 4 which is to be tested for defects within the material.

The probe 1 comprises a housing 10 containing a first wedge-shaped coupling element 11, also known as a delay line, a first ultrasonic transducer 12, a second wedge-shaped coupling element 13 and a second ultrasonic transducer 14.

Two electrodes 15, 16 are disposed on the two sides of the first transducer 12 and two electrodes 17, 18 are correspondingly disposed on the second transducer 14. Conductors 19 to 22 connect electrodes 15, 16, 17 and 18 to the cable 3.

The construction of a probe 1 according to the invention is based on a commercial 45° angle test probe (e.g. type WB45-2E produced by Krautkramer GmbH, Cologne, Federal Republic of Germany). A probe of this type contains a first coupling member 11, usually of Plexiglass, and an ultrasonic transducer 12. The wedge angle $\alpha_1$ of the delay element is chosen so that in the case of a steel workpiece 4, the acoustic wave transmission angle $\beta_1$ of the central ray 23 is at an angle of 45° to the axis normal to the workpiece surface. In the test probe type WB45-2E, the angle $\alpha_1 = 37°$.

A second wedge-shaped coupling element 13 is disposed on the first coupling element 11 and corresponding ultrasonic transducer 12, and a second ultrasonic transducer 14 is disposed on the coupling element 13. In the present example an aluminium coupling element 13 having a wedge angle $\alpha_2$ of 23.6 degrees was used. The acoustic wave transmission angle $\beta_2$ of the central ray 24, based on the laws of refraction at the interfaces of elements 13, 11 and at the interfaces of element 11 and workpiece 4 made of steel was 60 degrees.

The second coupling element 13 was adhesively fastened to the first coupling element 11, and the cavity 25 shown in FIG. 1 was filled with adhesive material. An epoxy adhesive was used.

For operation, the test angle (45° or 60°) was specified and the respective ultrasonic transducer 12 or 14 was actuated, by supplying each transducer with electric pulses from the ultrasonic test instrument 2 via conductors 19, 20, 21 and 22 respectively. The ultrasonic pulses from transducer 12 travelled via wedge-shaped coupling element 11 to the workpiece 4. On the other hand the ultrasonic pulses generated by transducer 14 first travelled through wedge-shaped coupling element 13 and then through transducer 12 into coupling element 11.

In order to minimize the amount of reflected sound waves at the interface between coupling element 13 and transducer 12, care must be taken that the characteristic acoustic impedance of element 13 and that of the transducer 12 are approximately of the same value.

As shown in FIG. 1, the sound exit points 26, 27 of central rays 23 and 24 are physically at different places. There is a corresponding difference in the exit surfaces of the corresponding sound beams (not shown in FIGS. 1 and 2).

Figure 2:
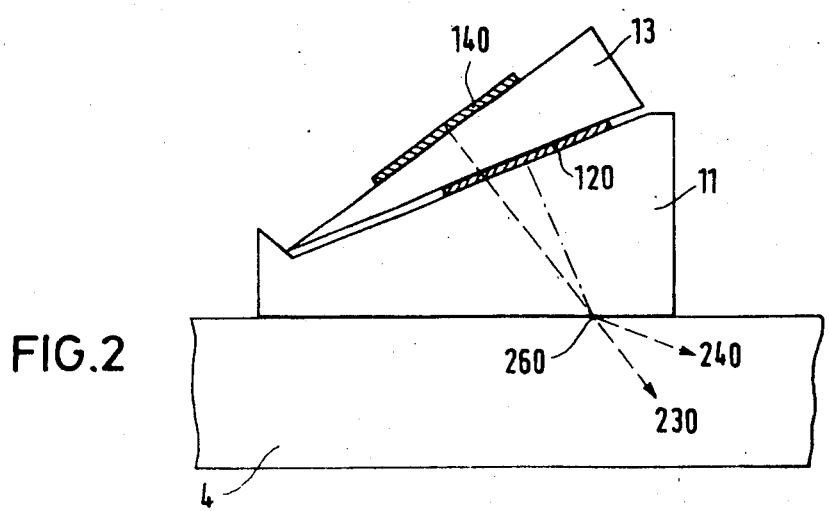
FIG. 2 is a view, similar to FIG. 1, but showing a modification.

However, the two ultrasonic transducers can be moved sideways to ensure that both central rays have the same sound exit point. This is shown in FIG. 2. The wedge-shaped coupling elements are denoted by numerals 11 and 13 as before and the corresponding ultrasound transducers are denoted by numerals 120 and 140. The central rays 230 and 240 travel through the same sound exit point 260.

Of course the invention is not limited to the above-described embodiment. For example, three or more ultrasonic transducers can be used instead of two. In that latter case, the transducers must be coupled to one another via a corresponding number of additional wedge-shaped coupling elements.

While there has been described and illustrated a preferred embodiment of the invention together with a modification thereof, it will be apparent to those skilled in the art that various further changes and modifications may be made therein without departing from the principle of this invention which shall be limited only by the scope of the appended claims.

What is claimed is:

1. An ultrasonic angle test probe including at least two ultrasonic transducers for respectively generating and receiving ultrasonic waves propagating at different angles of propagation in a workpiece to which the probe is acoustically coupled, the first ultrasonic transducer being disposed on a first wedge-shaped coupling element, the improvement comprising:

the second ultrasonic transducer disposed on a second wedge-shaped coupling element, and
said second coupling element being disposed on said first coupling element,
whereby ultrasonic waves generated and received by said second transducer travel through said first transducer along their path to and from the workpiece to which said probe is coupled.

2. An ultrasonic angle test probe as set forth in claim 1, said second transducer disposed on said second coupling element being disposed relative to said first transducer for causing both transducers to have substantially the same sound wave exit point on the probe side coupled to the workpiece.

* * * * *